United States Patent [19]

Monnier et al.

[11] Patent Number: 4,925,987

[45] Date of Patent: May 15, 1990

[54] PREPARATION OF ALDEHYDES FROM UNSATURATED TERMINAL EPOXIDES

[75] Inventors: John R. Monnier, Fairport; Howard M. Low, Rochester, both of N.Y.

[73] Assignee: Eastman Kodak Company, Rochester, N.Y.

[21] Appl. No.: 337,493

[22] Filed: Apr. 13, 1989

[51] Int. Cl.$^5$ .................. C07C 45/67; C07C 45/70
[52] U.S. Cl. .................................. 568/450
[58] Field of Search ................... 568/450, 427

[56] References Cited

U.S. PATENT DOCUMENTS

| | | | |
|---|---|---|---|
| 1,906,833 | 5/1933 | Baur | 568/450 |
| 2,503,050 | 4/1950 | Jacobs et al. | 568/450 |
| 2,601,538 | 6/1952 | Lundsted | 568/450 |
| 2,628,255 | 2/1953 | Sexton et al. | 568/450 |
| 2,686,205 | 8/1954 | Gasson et al. | 568/205 |
| 2,694,090 | 11/1954 | Wild et al. | 568/450 |
| 3,067,256 | 12/1962 | Fischer et al. | 568/450 |
| 3,465,043 | 9/1969 | Lini et al. | 568/450 |
| 4,495,371 | 1/1985 | Neri et al. | 568/450 |
| 4,621,150 | 11/1986 | Hirai et al. | 560/51 |
| 4,650,908 | 3/1987 | Pope | 568/450 |

FOREIGN PATENT DOCUMENTS 1036130  7/1966  United Kingdom ............... 568/450

OTHER PUBLICATIONS

Alper et al, J. Org. Chem. 41(22) pp. 3611–3613, (1976).

Primary Examiner—Werren B. Lone
Attorney, Agent, or Firm—Robert A. Linn

[57] ABSTRACT

Crotoaldehyde is produced by contacting butadiene monoxide with a metal oxide, mixed metal oxide, or mixture of metal oxides. The process is preferably conducted in the vapor phase. Other unsaturated aldehydes can be prepared from other unsaturated terminal epoxides.

10 Claims, No Drawings

PREPARATION OF ALDEHYDES FROM UNSATURATED TERMINAL EPOXIDES

FIELD OF THE INVENTION

This invention relates to a catalytic method for the preparation of unsaturated aldehydes. In the process, an unsaturated terminal epoxide is contacted with a metal oxide catalyst. In a particular aspect, the invention pertains to the preparation of crotonaldehyde by contacting butadiene monoxide with such a catalyst.

RELATED ART

Lini U.S. Pat. No. 3,465,043 teaches that crotonaldehyde can be made from butadiene monoxide in the presence of a rhodium-containing catalyst. The catalyst may be a compound such as bis-carbonyl rhodium (II) chloride dimer, or rhodium (III) chloride trihydrate.

Alper et al J. Org. Chem. 41(22) 3611-3613 teaches that vinyl epoxides give α, β-unsaturated aldehydes when contacted with a catalytic amount of molybdenum hexacarbonyl.

The above described prior art processes are not entirely satisfactory because of the nature of the catalysts employed. More particularly, the catalysts of the prior art are relatively expensive or relatively unsuitable because of their thermal and/or chemical instability. Hence, a need exists for a process for making unsaturated aldehydes from unsaturated epoxides using a catalyst which exhibits chemical and thermal stability, is readily available, and comparatively inexpensive. Until the present invention, it was not known that the materials used as catalysts in the present process could be used to prepare unsaturated aldehydes from unsaturated epoxides. Hence, it is believed that the present invention presents a significant advance in the art.

SUMMARY OF THE INVENTION

This invention relates to the preparation of unsaturated aldehydes from unsaturated terminal epoxides. The process involves opening of the epoxide ring, migration of a hydrogen radical from one ring carbon to another position to give a carbonyl group, and also a migration of a carbon to carbon double bond from one position in the molecule to another. The mechanism by which these multiple transformations take place is not known at this time.

Aldehydes are widely used as chemical intermediates. So are compounds with olefinic double bonds. Hence, the products of the instant invention are highly useful as intermediates since they contain both reactive systems, the aldehyde group and the olefinic linkage

DESCRIPTION OF PREFERRED EMBODIMENTS

This invention provides a process for the preparation of an unsaturated aldehyde, said process comprising isomerizing a terminal epoxide having an olefinically unsaturated carbon atom in a position which is adjacent to the epoxide ring in said epoxide, by contacting said epoxide with a catalytic quantity of a catalyst (preferably a supported catalyst) at a temperature at which said isomerization takes place, said catalyst comprising an oxide of a metal selected from Groups IIA, IIIA, IVA, IB, IIB, IVB, VB, VIB, VIIB, and the iron subgroup of the Periodic Table. Preferred oxides are composed solely of one or more metals and oxygen.

The terminal, unsaturated epoxides employed in the process of this invention have the formula

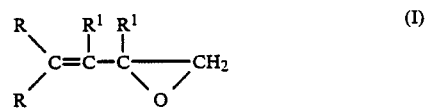

wherein the substituents indicated by R and $R^1$ are hydrogen, or organic substituents which do not interfere with the process. The organic substituents preferably (i) are stable of substantially stable under the reactions employed, (ii) are unreactive or substantially unreactive with the catalyst, the product, and other moieties within molecules of the starting epoxide, and (iii) do not interfere with the process by steric hindrance, or by poisoning the catalyst, or by some other undesired mechanism. For the purpose of this invention, such substituents meeting or the above three criteria are designated "inert substituents".

As indicated above, when all substituents illustrated by R and $R^1$ in the above structural formula are hydrogen, the compound is the material referred to herein as "butadiene monoxide". The invention is not critically dependent on the nature of the substituents bonded to the carbon atoms. A wide variety of substituents may be present, provided that they effectively meet the criteria set forth above. It is preferred that the moieties indicated by R in the above formula be selected from the hydrogen radical and alkyl radicals that have up to about 4 carbon atoms and the substituents represented by $R^1$ be selected from hydrogen and alkyl groups having up to about two carbon atoms. Other alkyl groups can also be used, if desired. As already indicated, a highly preferred reactant is butadiene monoxide.

The products of this invention are unsaturated aldehydes:

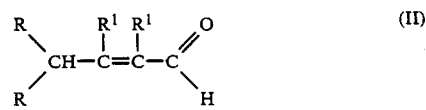

wherein R and $R^1$ have the same significance as above.

The catalyst employed in the process of this invention can be selected from a wide variety of metal oxides, particularly binary metal oxides, mixed metal oxides, and mixtures of metal oxides comprising oxides of the metals mentioned above. Thus for example, the catalyst may be selected from oxides of a Group IB metal such as copper or silver, or a Group IIB metal such as zinc or cadmium.

The catalyst employed is heterogeneous, i.e., not soluble in the reaction mixture. The catalyst can be used in a reaction with gaseous or liquid reaction systems. When desired, the reaction mixture can contain an inert liquid reaction medium to facilitate contacting the reactants, e.g., when the olefin oxide is a solid at reaction temperature. The reaction medium may be selected from liquid hydrocarbons or ethers, such as hexanes or tetrahydrofuran The above catalytic materials may also be applied to a solid support for efficient use of the catalyst, although in some cases the catalytic materials may also be considered as catalyst supports themselves. Inert supports commonly employed in the catalyst arts may be used.

When a catalyst support is employed, the loading level of the catalytic oxide on the support typically falls within the range of about 0.5 up to 50 weight percent, calculated as oxide and based on the total weight of finished catalyst. Preferably, the loading level of the catalyst falls within the range of about 1 up to 40 weight percent with loading levels in the range of about 1 up to 30 weight percent being most preferred.

The actual physical form of the catalyst support is not particularly important. While the form of the catalyst support has little effect on catalyst activity, Practical considerations such as ease of heat transfer, mass transfer, pressure drop due to fluid flow restrictions, efficiency of gas-liquid-solid contacting, catalyst durability, and the like make the use of defined shapes such as spheres, pellets, extrudates, rings, saddles, and the like, preferred catalytic materials.

Those of skill in the art will also recognize that catalysts employed in the practice of the present invention can include additional components which may modify catalyst activity and/or selectivity. Thus additives may be incorporated into the finished catalyst to aid catalyst preparation, e.g., binders, die lubricants, and the like; or to reduce the cost of catalyst preparation; or to extend the operating ranges for reaction temperature and/or pressure; or to increase catalyst lifetime under reaction conditions. It is recognized, of course, that some additives are suitably employed in very low levels (i.e., milligrams of additive per gram of catalyst); while other additives (i.e., binders, diluents, and the like) are suitably employed at significantly higher levels (i.e., as a significant percentage of the total catalyst weight).

Supported catalysts can be prepared employing techniques well known to those of skill in the art. e.g., by precipitation of the active materials on the support, by impregnation, by coprecipitation of support and active materials by grinding together solid support and active material(s) in particulate form. In some instances, materials must be calcined, i.e. (heated in air or an oxygen-enriched gas phase under conditions in order to transform the supported species into its oxide form, which is the active state of the catalyst.)

The process temperature, pressure and contact time of the catalytic reaction are not critical. One uses a temperature at which isomerization to form the desired product takes place. The process can be conducted at any convenient pressure. The reaction (contact) time is not a truly independent variable, but is dependent at least to some extent on the other reaction variables employed, such as the process temperature, the inherent reactivity of the epoxide, the activity of the catalyst, etc. The process temperature, pressure, and time of reaction are discussed in more detail below.

Suitable reaction temperatures generally fall within the range of about 100° C. up to about 350° C. At lower temperatures, the reaction may proceed so slowly as to be impractical, while at higher temperatures undesirable levels of by-products, e.g. carbon dioxide, might be obtained. Preferred reaction temperatures fall within the range of about 110° C. up to 300° C.

The reaction pressure can be within a wide range. Typically pressures of about 0.1 to about 100 atmospheres are chosen, primarily as a function of safety, handling, equipment limitations and other practical consideration. Preferably, the reaction pressure is maintained in the range of from about 1 to about 30 atmospheres.

Because the process of this invention is exothermic in many instances it is preferred that the epoxide not be contacted neat with the catalyst. In other words, it is preferred that the epoxide be admixed with a diluent. Suitable diluents are inert under the reaction conditions employed. Examples of diluent gases useful in this invention include methane, ethane, nitrogen, helium, argon, neon, carbon dioxide, and the like. It is preferred that the partial pressure of the epoxide be in the range of from about 0.01 to about 0.5. When the process is conducted in the liquid phase, a saturated hydrocarbon can be used as the inert reaction medium. Any convenient concentration of epoxide in the inert liquid can be used, e.g. from about 0.1 to 50 weight percent.

A wide range of contact times can be used for the practice of the present invention within wide ranges. Generally, the epoxide and catalyst are maintained in contact for a time sufficient to obtain epoxide conversions in the range of about 0.5 up to 95 mole percent or higher. Epoxide conversions can be varied to give the most efficient utilization of reactor capacity.

Those of skill in the art recognize that the actual contact times required to accomplish the desired conversion levels can vary within wide ranges, depending on such factors as vessel size, epoxide to diluent ratios, the loading level on the catalyst, the presence or absence of any catalyst modifiers (and their loading levels), the reaction temperature and pressure, and the like.

The invention process can be carried out in either batch or continuous mode. Continuous reaction is presently preferred since high reactor throughout and higher purity product is obtained in this manner. The batch mode is satisfactorily employed when high volume of reactant throughout is not required, for example, for liquid phase reactions.

For continuous mode of reaction carried out in the gase phase, typical gas hourly space velocities (GHSV) fall within the range of about 100 up to 30,000 $hr^{-1}$. GHSV in the range of about 200 up to 20,000 $hr^{-1}$ are preferred, with GHSV in the range of about 300 up to 10,000 $hr^{-1}$ being most preferred.

When a continuous mode of reaction is carried out in the liquid phase, typical liquid hourly space velocities (LHSV) employed will give contact times analogous to that obtained at the GHSV values given above. Most preferably, LHSV employed will fall in a range so as to produce a desirable combination of feed epoxide conversion levels and high product selectivity.

Recovery of product produced in the practice of the present invention can readily be carried out employing techniques well known by those of skill in the art. For example, where reaction is carried out in the continuous mode, unreacted starting material is initially separated from reaction products; and the desired product then isolated from the resulting product mixture by distillation, crystallization, extraction, or the like.

EXAMPLES

In all of the following runs, the processes were carried out under steady state conditions in a one atmosphere, single-pass flow reactor system. The reactor tube was constructed of Pyrex, and the catalyst charge (between 0.1 and 20 grams) was held in place by means of a Pyrex frit. The reactor tube was housed inside a vertical, split tube furnace controlled by a temperature controller, which maintained the reaction temperature over the desired range. All feed inlet lines and reactor exit lines were maintained at 120° C. to prevent condensation of feed or product components. The geometric design of the reactor and of the catalyst particles, as well as the bed depth were chosen to maintain and measure the true kinetic and catalytic aspects of the reaction being investigated. Gas hourly space velocities for all experiments fell within the range of from 100 to 3000 hr$^{-1}$. A chromel/alumel thermocouple sheathed in stainless steel was embedded within the catalyst bed to measure the actual temperature of reaction.

The epoxide feed, butadiene monoxide, was added as a vapor by bubbling helium, (an inert carrier gas) through a liquid/vapor saturator maintained at constant temperature to ensure constant and reproducible partial pressure of the epoxide in the helium stream. The temperature of the saturator was held constant at a pre-selected temperature within the range of from $-10°$ C. to $20°$ C., to give partial pressure of the epoxide vapor within the range of from 0.03 to 0.17 atmosphere, in the helium diluent. The helium flow rate was maintained by using a mass flow controller. The device permitted accurate and reproducible helium flow rates in the range of 0-200 ml (STP)/min.

Reaction product analysis, and analysis of the feed composition, were made using an in-line, gas sampling loop connected directly to the inlet of a Varian 3760 gas chromatograph. Unreacted feed and reaction products were separated using a packed Pyrex glass column (eight feet long and 2mm internal diameter) of Chromasorb 102 porous polymer packing. A flame ionization detector gave quantitative analysis of the various reaction products. In many instances, the feed epoxide and the crotonaldehyde were the only organics present in the product stream.

Results and reaction conditions are summarized in the following table. The catalysts which were used were given no special pretreatment other than a thermal soak at $150°$ C. in flowing helium before exposure to the feed epoxide and helium diluent at the specified conditions.

a nominal composition of 11.5% Ba, 27.5% Cr, 33.5% Cu, with the balance being oxygen. It is denoted by UCI as G-22.

Catalyst 3, also supplied by UCI and denoted as G-89, has the composition $CuO-BaCrO_4-CuCr_2O_4$ and a nominal composition of 38% Cu, 33% Cr, 3.5% Mn, with the balance being oxygen.

Catalyst 4 is $MoO_3$ powder (Catalog No. 302684) supplied by Alfa Products, 152 Andover St., Danvers, Ma.

Catalyst 5 which is denoted as $CuO/Al_2O_3$, consists of CuO which has been supported on $Al_2O_3$. The "slash" indicates that CuO is supported on $Al_2O_3$. This is different from a mixture of CuO and $Al_2O_3$. Catalyst 5, which contained 10-12% Cu (by weight) was supplied by Strem Chemicals, 7 Mulliken Way, P.O. Box 108, Newburyport, Ma. This catalyst is designed as 29-0650 in the Strem Catalog.

Catalyst 6 is $CuAl_2O_4$ and is a mixed oxide phase which was prepared by calcining catalyst 5 in air at $1000°$ C. for 5 hours.

Catalyst 7 which is $CuCO_3$ supported on $SiO_2$ is denoted as $CuCO_3/SiO_2$. This catalyst was also supplied by Strem Chemicals (Catalog No. 29-0280) and contains 6% Cu by weight.

Oftentimes mixed metal catalyst are more stable toward reduction than simple oxides. Also, they can be more acidic. In many instances, mixed metal oxides are more reactive. The increased activity may be attributable to greater surface area or the formation of unique catalytic sites.

The copper carbonate catalyst denoted as Catalyst 7 can also be transformed into copper oxide by heating at a temperature of about $200°$ C. or higher.

The processes employed in the above examples can be extended to the use of 4,4-dimethylbutadiene monoxide, and other dialkyl butadiene monoxides where the alkyl groups are in the positions noted as R and R$^1$ in

TABLE

| Catalyst Number % | Catalyst Composition | Temp. °C. | GHSV, hr$^{-1}$ | Butadiene Monoxide Conversion | Crotonaldehyde* Selectivity, % |
|---|---|---|---|---|---|
| 1 | CuO—ZnO | 125 | 800 | 21 | 100 |
| 2 | CuO—BaCrO$_4$—CuCr$_2$O$_4$ | 132 | 1500 | 2 | 99 |
|  |  | 153 | 1500 | 5 | 99 |
|  |  | 255 | 1500 | 10 | 93 |
|  |  | 280 | 1500 | 14 | 87 |
| 3 | CuO—Mn$_3$O$_4$—CuCr$_2$O$_4$ | 190 | 2000 | 48 | 92 |
| 4 | MoO$_3$ | 127 | 800 | 4 | 100 |
|  |  | 152 | 800 | 91 | 99 |
| 5 | CuO/Al$_2$O$_3$ | 120 | 1500 | 37 | 97 |
| 6 | CuAl$_2$O$_4$ | 175 | 1500 | 83 | 97 |
| 7 | CuCO$_3$/SiO$_2$ | 131 | 750 | 12 | 98 |

*Selectivity expressed as molar selectivity, i.e., moles of crotonaldehyde formed based on moles of butadiene monoxide converted.

Catalyst 1 is an intimate mixture of CuO and ZnO having a nominal composition of CuO/ZnO=$\frac{1}{2}$. This catalyst was supplied by United Catalyst Inc. (UCI), P.O. Box 32370, Louisville, Ky., and is denoted as C18-0 in their Catalyst Brochure. This catalyst, which exists as a mixture of metal oxides will be represented as CuO-ZnO, whereby the "dash"indicates the existence of a homogeneous and intimate mixture of the components connected by the "dash". This formalism will be used for all other invention catalyst which exist as mixtures.

Catalyst 2 is a homogeneous mixture of CuO+-BaCr$_4$+CuCr$_2$O$_4$ and is denoted as CuO—BaCrO$_4$—CuCr$_2$O$_4$. This catalyst which was supplied by UCI, has Formula (I). Examples include dimethylbutadiene monoxide up to and including di-n-butyl-butadiene monoxides can also be used. The feed epoxides can admixed with methane, ethane, nitrogen, carbon dioxide, or helium as an inert gaseous diluent, such that the partial pressure of the olefin epoxide is from 0.01 to 0.5. Using the above feed compositions, a temperature of $100-350°$ C., and a reaction pressure of 0.1 to 100 atmospheres, the corresponding aldehyde is produced using as a catalyst, a metal oxide of Groups IIA, IIIA, IVA, IB, IIB, IVB, VB, VIB, VIIB, and the iron subgroup of the Periodic Table.

The invention has been fully described above with particular reference to preferred embodiments, it will be understood that modifications and substitutions thereof can be made without departing from the scope and spirit of the appended claims.

We claim:

1. Process for the preparation of an unsaturated aldehyde, said process comprising isomerizing a terminal epoxide having an olefinic double bond on a carbon atom adjacent to a carbon atom in the epoxide ring, said epoxide having the formula:

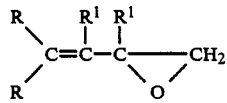

wherein each substituent indicated by R is selected from the class consisting of hydrogen and alkyl radicals having up to about four carbon atoms, and each substituent indicated by $R^1$ is selected from the hydrogen and alkyl groups of up to about two carbon atoms.

said process comprising contacting said epoxide at a temperature within the range of from about 100° C. to about 350° C., with a catalytic quantity of a catalyst selected from binary metal oxides, mixed metal oxides, and mixtures of oxides of a Group IB or IIB metal;

said unsaturated aldehyde product having the formula:

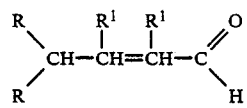

wherein R and $R^1$ each have the same significance as above.

2. The process of claim 1 wherein said epoxide is selected from butadiene monoxide and dimethyl butadiene monoxide.

3. Process of claim 2 wherein said terminal epoxide is butadiene monoxide.

4. Process of claim 1 wherein said catalyst is on a support, and the loading level of the catalytic oxide is within the range of 0.5–50 weight percent, calculated as oxide, and based on the total weight of finished catalyst.

5. Process of claim 4 wherein the reaction pressure is from about 0.1 to about 100 atmospheres.

6. Process of claim 1 wherein said terminal epoxide is contacted with said catalyst in the vapor phase in the presence of a diluent, such that the partial pressure of the epoxide is from about 0.01 to about 0.5.

7. Process of claim 6 wherein the gas hourly space velocity is within the range of from about 100 to about 30,000 $hr^{-1}$.

8. Process for the preparation of an unsaturated aldehyde, said process comprising isomerizing a terminal epoxide having an olefinic double bond on a carbon atom adjacent to a carbon atom in the epoxide ring, said epoxide having the formula:

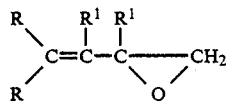

wherein each substituent indicated by R is selected from the class consisting of hydrogen and alkyl radicals having up to about four carbon atoms, and each substituent indicated by $R^1$ is selected from hydrogen and alkyl groups of up to about two carbon atoms, said process comprising contacting said epoxide at a temperature within the range of from about 100° C. to about 350° C., with a catalytic quantity of a catalyst selected from CuO-ZnO, CuO-BaCrO$_4$-CuCr$_2$O$_4$, CuO-Mn$_3$O$_4$-CuCr$_2$O$_4$, MoO$_3$, CuO/Al$_2$O$_3$, CuAl$_2$O$_4$, and CuCO$_3$/SiO$_2$;

said unsaturated aldehyde product having the formula:

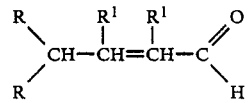

wherein R and $R^1$ each have the same significance as above.

9. Process of claim 8 wherein said terminal epoxide is butadiene monoxide.

10. Process of claim 8 wherein said epoxide is contacted with said catalyst in the vapor phase with a diluent at a pressure within the range of from about one to about 30 atmospheres.

* * * * *